US 6,323,035 B1

(12) United States Patent
Kedar et al.

(10) Patent No.: US 6,323,035 B1
(45) Date of Patent: *Nov. 27, 2001

(54) SYSTEMS AND METHODS FOR HANDLING AND MANIPULATING MULTI-WELL PLATES

(75) Inventors: Haim Kedar, Palo Alto; Albert William Brown, Jr., San Jose, both of CA (US)

(73) Assignee: Glaxo Wellcome, Inc., Research Triangle Park, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/937,139

(22) Filed: Sep. 24, 1997

(51) Int. Cl.[7] ............................... G01N 35/00; B25J 7/00
(52) U.S. Cl. ................................. 436/43; 436/43; 436/47; 436/49; 422/63; 422/65; 422/102; 422/104; 414/277; 414/281; 414/807
(58) Field of Search .................................. 422/63, 65, 50, 422/81, 68.1, 104; 435/288.3, 288.4; 436/43, 47, 49; 414/277, 281, 807

(56) References Cited

U.S. PATENT DOCUMENTS 3,650,306 * 3/1972 Lancaster ........................ 141/238
4,396,579 * 8/1983 Schroeder et al. ................ 422/52
4,493,815 * 1/1985 Fernwood et al. .

(List continued on next page.)

FOREIGN PATENT DOCUMENTS

WO 92/22800   12/1992 (WO).
WO 96/30761 * 10/1996 (WO).
WO 96/33010 * 10/1996 (WO).
WO 97/11352    3/1997 (WO).

OTHER PUBLICATIONS

Brochure, "Millipore MultiScreen Assay System," Millipore Corporation, Bedford, MA 01730, Rev. B 9/91, 14 pages.*
DeWitt and Czarnik (1995), Current Opinion in Biotechnology 6:640–645, "Automated synthesis and combinatorial chemistry." *
Lashkari et al. (1995), Proc. Natl. Acad. Sci. USA 92:7912–7915, "An automated multiplex oligonucleotide synthesizer: Development of high–throughput, low–cost DNA synthesis." *
Multiblock—Instrument for multiple and combinatorial synthesis—Brief Description and User's Manual, 5 pages.*
Myers et al., "Multiple simulataneous synthesis of phenolic libraries," ESCOM Science Publishers B.V., Leiden, The Netherlands, Copyright 1995, 16 pages.*
Product Brochure for a reaction block for "Combinatorial Chemistry," by SyRo, 1 page.*
Product Brochure, "ALCHEMY 2000 Automated Reaction System," Sagian Incorporated, 3 pages.*

Primary Examiner—Jill Warden
Assistant Examiner—Kathryn Bex
(74) Attorney, Agent, or Firm—Townsend and Townsend and Crew LLP (57) ABSTRACT

The invention provides exemplary systems, devices and methods for manipulating and handling multi-well plates. In one exemplary embodiment, a system is provided which comprises a robot having a base member and at least one arm. The arm includes a grasping mechanism which is adapted to grasp the plate. Further, the grasping mechanism is configured to receive the plate in a repeatable and known location such that the location of each well relative to the grasping mechanism is known by the robot.

11 Claims, 7 Drawing Sheets

U.S. PATENT DOCUMENTS

| | | |
|---|---|---|
| 4,526,690 * | 7/1985 | Kiovsky et al. . |
| 4,908,320 * | 3/1990 | Zakowski et al. ............ 436/45 |
| 4,971,514 | 11/1990 | Hunter . |
| 4,981,801 | 1/1991 | Suzuki et al. . |
| 5,108,704 * | 4/1992 | Bowers et al. . |
| 5,167,922 * | 12/1992 | Long ............................. 422/58 |
| 5,219,528 * | 6/1993 | Clark . |
| 5,288,464 * | 2/1994 | Nokihara . |
| 5,324,483 * | 6/1994 | Cody et al. . |
| 5,332,549 * | 7/1994 | MacIndoe, Jr. ............... 422/63 |
| 5,416,329 | 5/1995 | Sonne et al. . |
| 5,455,008 * | 10/1995 | Earley et al. ............... 422/100 |
| 5,456,882 * | 10/1995 | Covain ........................ 422/64 |
| 5,460,783 * | 10/1995 | Hautea et al. ............... 422/104 |
| 5,470,744 * | 11/1995 | Astle ........................... 435/286.7 |
| 5,518,686 * | 5/1996 | Masterson et al. ............ 422/63 |
| 5,620,894 * | 4/1997 | Barger et al. . |
| 5,645,800 | 7/1997 | Masterson et al. . |
| 5,686,047 * | 11/1997 | Augstein ...................... 422/65 |
| 5,738,827 * | 4/1998 | Marquiss ..................... 422/104 |

* cited by examiner

SYSTEMS AND METHODS FOR HANDLING AND MANIPULATING MULTI-WELL PLATES

BACKGROUND OF THE INVENTION

The invention relates generally to the field of device handling and manipulation, and particularly to the handling and manipulation of multi-well plates. In one particular aspect, the invention provides for the transport of multi-well plates to precise and known locations at various processing or evaluation stations.

The use of multi-well plates to facilitate the performance of various chemical and biological procedures has become widely accepted. Such multi-well plates are typically rectangular in geometry and have a two dimensional array of wells. For example, one common multi-well plate design has an 8 by 12 array of wells.

To accommodate the performance of various procedures, the wells of such plates are configured to receive various chemicals or substances. One common procedure is the performance of assays where various chemicals or substances are introduced into the wells and any reactions are evaluated. One type of assay evaluation may proceed by placing the plate above a camera to detect an emitted signal from the wells.

Hence, when using such multi-well plates, it is often desirable to efficiently deliver and/or remove various chemicals or substances into or from the wells. This often requires the plate to be moved to various pieces of processing equipment for filling or removal. Further, the plates may also need to be transported to evaluation equipment for detection or other evaluation.

When introducing or removing fluids or substances into or from the wells, and when evaluating the substances within the wells, the wells typically need to be aligned with distal tips, detection devices and the like. However, since various pieces of equipment may be needed to complete a procedure, each time the plate is moved to a different piece of equipment, the plate will need to be properly oriented according to the specifications of the given piece of equipment. For example, many types of fluid delivery equipment include a stage on which the plate is placed. Often a robot is employed to grasp the plate and move the plate to the stage. However, such robots typically have a pair of grasping fingers which grasp the plate in an arbitrary manner and then place the plate on the stage.

Hence, once on the stage and removed from the robot, the dispensing tips will need to be aligned with the wells in the plate. Such a system is often burdensome and time consuming. Moreover, as it becomes more desirable to increase the numbers of wells in the plate while reducing their size, it becomes more difficult to precisely align the wells with various pieces of equipment. For example, many types of filling equipment are provided with 96 dispensing tips. If an 864 well plate is placed on a stage which can move only in the vertical direction, it is difficult, if not impossible, for the 96 dispensing tips to fill all of the 864 wells while the plate remains fixed on the stage.

Hence, it would be desirable to provide systems, devices and methods to facilitate the transport of multi-well plates between various pieces of equipment in a manner such that the wells may be efficiently accessed or evaluated.

SUMMARY OF THE INVENTION

The invention provides exemplary systems, devices and methods for handling multi-well plates. In one exemplary embodiment, the invention provides a system for handling a plate having a plurality of wells and comprises a robot having a base member and at least one arm. The arm includes a grasping mechanism which is adapted to grasp the plate. Further, the grasping mechanism is configured to receive the plate in a repeatable and known location such that the location of each well relative to the grasping mechanism is known by the robot.

The robot of the invention is particularly useful in combination with a plurality of stations which are positioned at known locations relative to the robot. In this way, a processor that is associated with the robot may be configured to control movement of the robot to place the plate at predetermined locations at the stations. For instance, some of the stations may include processing equipment having an array of delivery lines to allow fluids or substances to be introduced into the wells when the plate is at the predetermined locations. In this way, the plate may remain attached to the robot and be precisely aligned with the various delivery lines during a given procedure.

As one example, the plate may include 864 wells that are to be filled by a piece of equipment having 96 dispensing tips. Since the location of the wells is known to the robot relative to the dispensing tips, the robot may move the plate to nine different locations to allow all of the 864 wells to be filled. Once filling is finished, the robot may move the plate to another station where other procedures may be performed in a similar manner.

In one particular aspect, the arm comprises a shaft, an elbow attached to the shaft, and a linkage pivotally attached to the elbow. With such a configuration, the grasping mechanism is operably attached to the linkage. In another aspect, the shaft is rotatable relative to the base member and is also movable in a vertical direction. The linkage is pivotable relative to the elbow to move the grasping mechanism radially outward from the base member.

In one particularly preferable aspect, the grasping mechanism comprises a frame member having edges which are adapted to frame at least a portion of a periphery of the plate in a repeatable and predictable manner so that the location of the wells of the plate relative to the frame member is known when the plate is received into the frame member. The grasping mechanism further includes a securing mechanism for securing the plate to the frame member when the plate is received within the frame member.

In one exemplary aspect, the system further includes a rack having a plurality of patterned shelves for housing a plurality of plates. With such a configuration, the frame member is provided with a patterned opening to allow the grasping mechanism to grasp a plate from the rack by positioning the frame member below one of the shelves having the desired plate and upwardly moving the frame member until the frame member lifts the plate from the shelf. During the upward movement of the frame member, the shelf passes through the patterned opening. To replace a plate, the frame member is lowered until the patterned opening passes over the patterned shelf, with the patterned shelf lifting the plate from the frame member.

The securing mechanism preferably comprises a clamping arm that is pivotally attached to the frame member and which is adapted to engage a portion of the periphery of the plate. Such a clamping arm is particularly useful when the plate is generally rectangular in geometry. With such a plate geometry, the edges of the frame member are preferably configured to engage at least two sides of the plate while the clamping arm engages a corner of the plate that is located at an intersection of the other two sides of the plate. The clamping arm thus secures the plate against the edges of the frame member.

In one particular aspect, at least some of the edges of the frame member which are adapted to engage the plate are inwardly tapered to assist in securing the plate to the frame member. Similarly, an edge of the clamping arm may also be tapered. Such tapering serves to prevent vertical movement of the plate when clamped to the frame member.

In still another aspect, an attachment member is operably attached to the frame member to facilitate attachment to the arm of the robot. In yet another aspect, a translation mechanism is provided for axially translating the frame member. In this way, the grasping mechanism may be laterally moved relative to the arm of the robot.

The invention further provides an exemplary method for handling a plate having a plurality of wells. According to the method, a robot is provided having a base member and at least one arm which includes a grasping mechanism. A plate having a plurality of wells is grasped with the grasping mechanism such that the location of each well in the plate relative to the grasping mechanism is known by the robot.

Once grasped, the plate is moved with the robot to a predetermined location at a station. In this manner, the location of the wells of the plate relative to the station is known so that fluids or substances may be transferred into or removed from the wells. For example, the station may comprise a processing station which has delivery lines for introducing fluids into the wells or aspirating fluids from the wells. When the plate has more wells than fluid delivery lines, the invention provides for introducing fluids into a first group of the wells while the plate is at a first predetermined location. The plate is then moved with the robot to a second predetermined location at the processing station and fluids are introduced into a second group of the wells.

Further, the plate may be moved with the robot to a predetermined location at another processing station to allow a sample to be introduced into the wells while the plate is at the predetermined location. As another example, the station may comprise an evaluation station to allow the wells to be imaged with a camera while the plate is at the predetermined location. Preferably, the wells are aligned with pixels of the camera when the plate is at the predetermined location.

In still another aspect, a plurality of plates may be stored on shelves of a rack. In this way, the robot may move the grasping mechanism to grasp one of the plates from the rack.

DETAILED DESCRIPTION OF THE SPECIFIC EMBODIMENTS

The invention provides exemplary systems, devices and methods for handling and manipulating multi-well plates. In particular, the invention provides a robot having an arm with a grasping mechanism which is configured to grasp a multi-well plate in a repeatable and predictable manner such that the location of the wells relative to the robot is known each time the plate is grasped. The grasping mechanism is configured such that each time a plate is grasped, it will be received at a precise location on the grasping mechanism so that the robot will know the precise location of each of the wells.

The robot of the invention will preferably be included in a work cell having various pieces of processing and/or evaluation equipment which are positioned at known locations relative to the robot. In this way, the robot may be employed to move the plate to the various pieces of equipment and then align the wells with appropriate parts of the equipment. Such a system thus eliminates, if desired, the need to place the plate on stages that are commonly incorporated into the various pieces of equipment. In this manner, the processing and evaluation equipment may be simplified, thereby reducing costs and simplifying the process. Further, by using a relatively simple robot, the robot may be easily programmed to move the plate to the various pieces of equipment.

The invention may be used with a wide variety of multi-well plates, and will find its greatest use with multi-well plates having outer dimensions that are similar to the outer dimensions of most commercially available 96 well plates, typically having a length of about 12.8 cm and a width of about 8.6 cm. The invention will be particularly useful with multi-well plates with more than 96 wells, such as 384 well plates, 864 well plates, 1536 well plates, and the like, while still having the same outer dimensions as standard 96 well plates. For instance, one type of 864 well plate which may be used with the invention is described in co-pending U.S. application Ser. No. 08/868,689, filed Jun. 4, 1997, the disclosure of which is herein incorporated by reference. The invention is particularly useful with multi-well plates having more than 96 wells because the robot is able to move the wells into alignment with pieces of equipment that are designed for 96 well plates. In this way, the robot provides a way to use plates having larger numbers of wells with commercially available equipment originally designed for only 96 wells. Moreover, by providing a grasping mechanism which can repeatably grasp a multi-well plate in a precise location on the grasping mechanism, the position of each well relative to the robot will be known with precision. The robot may then be employed to accurately align the wells with various pieces of equipment. Such accurate alignment is particularly important when the plate has more than 96 wells because the well sizes will be relatively small. If the wells are not precisely aligned, proper filling or processing will not be possible.

Figure 1:
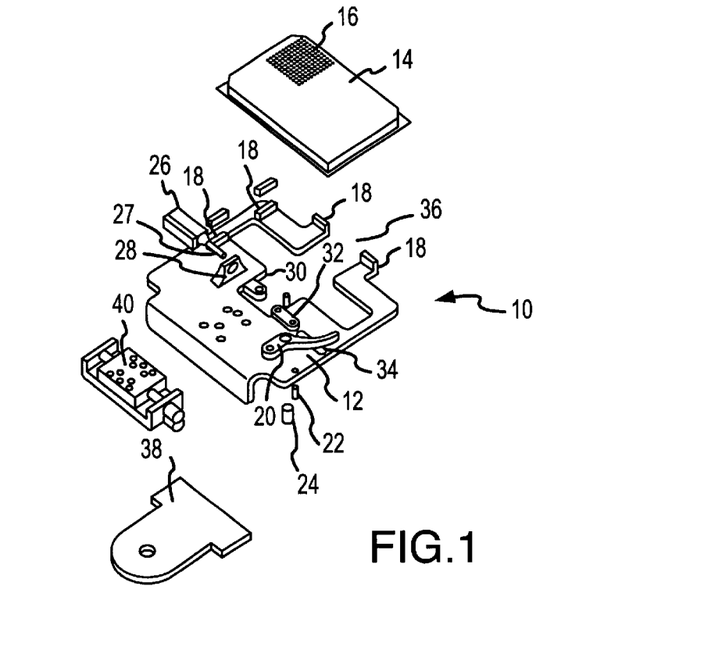
FIG. 1 is an exploded perspective view of an exemplary grasping mechanism according to the invention.
Figure 2:
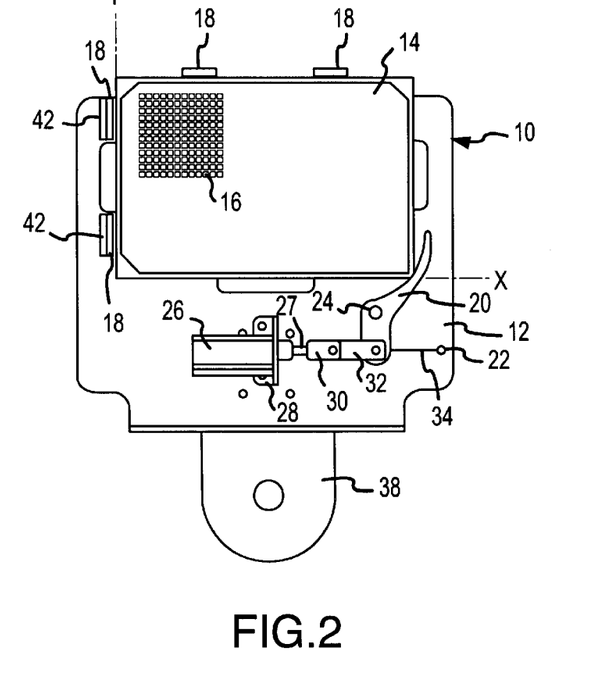
FIG. 2 is a top view of the grasping mechanism of FIG. 1.
Figure 3:
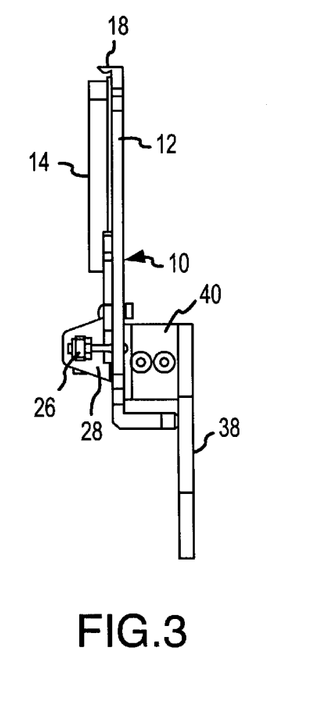
FIG. 3 is a side view of the grasping mechanism of FIG. 1.

Referring now to FIGS. 1–3, an exemplary embodiment of a grasping mechanism 10 which is useful in connection with a robot will be described. Grasping mechanism 10 comprises a frame member 12 which is configured to receive a multi-well plate 14. Multi-well plate 14 includes a plurality of wells 16 which are arranged in a two dimensional array (for convenience of illustration, only a selected number of the wells are shown).

Frame member 12 includes four raised edges 18 which serve as stops when plate 14 is forced against them. Edges 18 are arranged such that they will engage two sides of plate 14 when plate 14 is grasped. A clamping arm 20 is pivotally attached to frame member 12 in a manner such that it may be forced against a corner of plate 14. As clamping arm 20 pushes against the corner, it forces plate 14 against edges 18 to secure plate 14 to a precise location relative to frame member 12.

Edges 18 and clamping arm 20 are inwardly tapered as they approach frame member 12. In this way, when clamping arm 20 is pivoted against the corner, plate 14 will be forced downward against frame member 12. Hence, the location of plate 14 relative to frame member 12 will be secured in the X, Y and Z directions. In this manner, grasping mechanism 10 can be used with a wide variety of plates having standard sized outer dimensions and formats since the location of each well can be repeatably and precisely fixed relative to frame member 12.

Clamping arm 20 is pivotally attached to frame member 12 by an arm shaft 24. To pivot clamping arm 20 relative to frame member 12, an air actuated piston 26 having a rod 27 in combination with a spring 34 is employed. Piston 26 is attached to frame member 12 by a mount bracket 28, and spring 34 is attached to an arm post 22 on frame member 12. Between piston 26 and clamping arm 20 is a clevis 30 and a linkage 32. With such a configuration, spring 34 (which is in tension) causes clamping arm 20 to pivot about shaft 24 to apply a force against the corner of plate 14 as previously described. To release clamping arm 20, piston 26 is actuated to causing rod 27 to retract. In this manner, clamping arm 20 is pivoted in an opposite direction to release it from plate 14. As rod 27 of piston 26 retracts, spring 34 expands to allow clamping arm 20 to pivot.

As best shown in FIG. 1, frame member 12 includes a patterned opening 36. As described in greater detail hereinafter, patterned opening 36 is adapted to allow frame member 12 to pass over a patterned shelf when grasping plate 14.

Grasping mechanism 10 further includes an attachment member 38 which allows grasping mechanism 10 to be operably attached to a robot. Mounted to attachment member 38 is a linear translator 40 which moves frame member 12 in an axial direction. For instance, as illustrated in FIG. 2, linear translator 40 is able to move frame member 12 parallel to an X axis. In this way, once plate 14 is positioned at a piece of equipment, linear translator 40 may be employed to precisely move wells 16 into alignment with a set of dispensing tips or syringes as described in greater detail hereinafter.

Attached to two of the edges 18 is an alignment extension 42 which tapers away from the inner surfaces of edges 18. In this way, when frame member 12 is moved upward to grasp a plate, alignment extensions 42 will assist in funneling the plate into alignment with edges 18.

Figure 4:
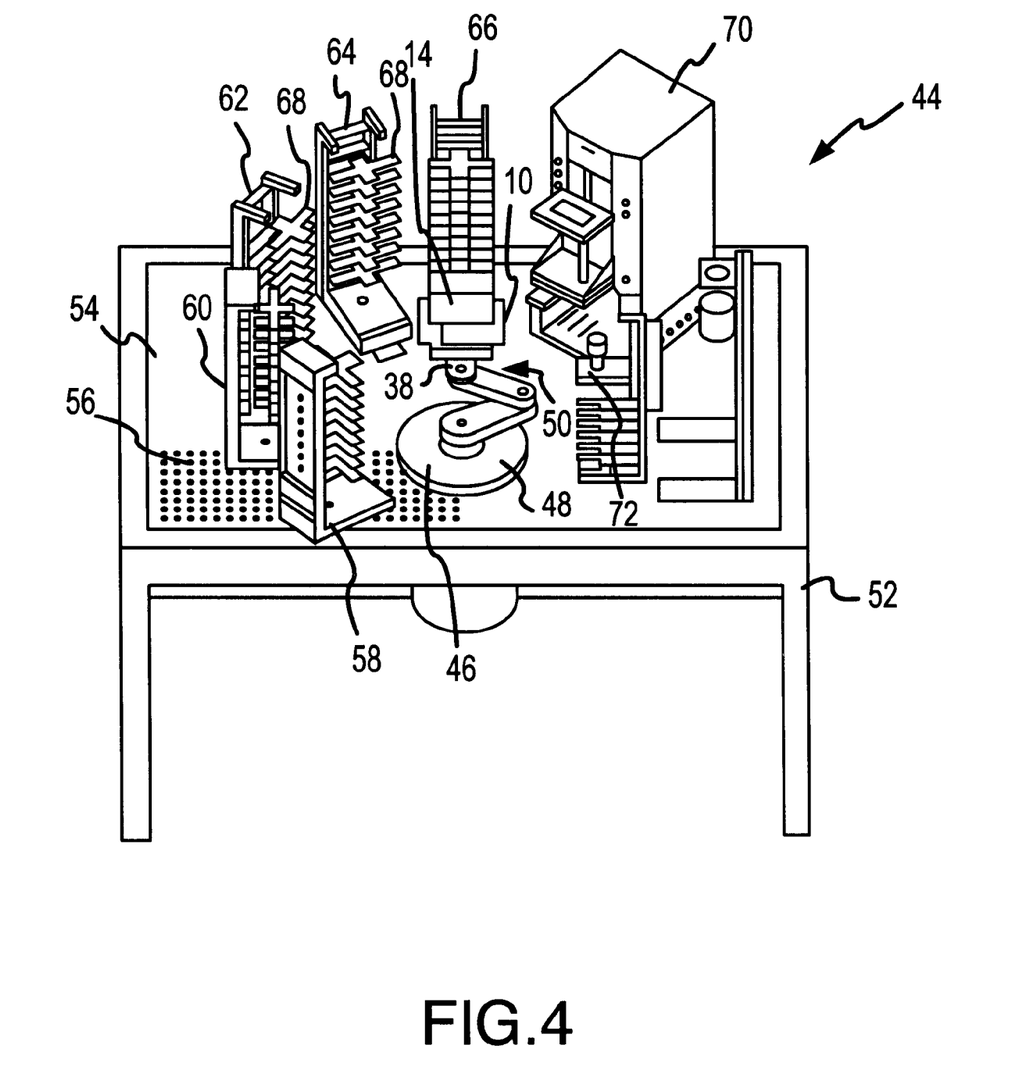
FIG. 4 is a perspective view of an exemplary plate handling system having a robot which employs the grasping mechanism of FIG. 1 according to the invention.
Figure 4A:
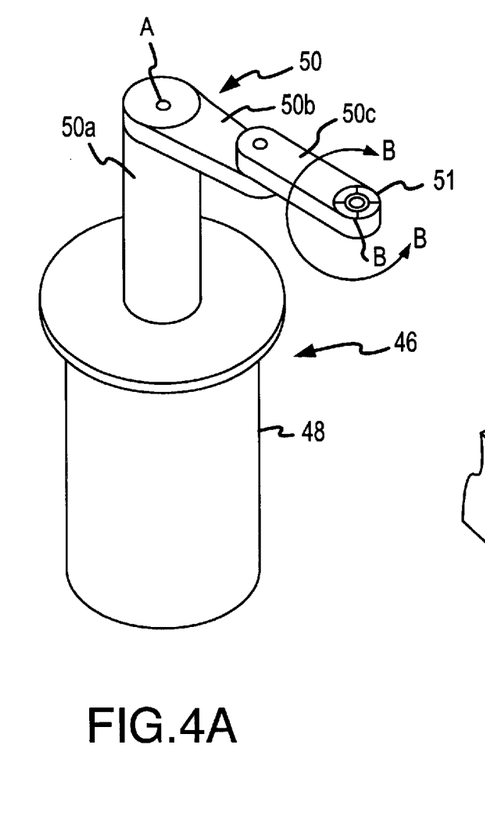
FIG. 4A is a perspective view of the robot of FIG. 4.
Figure 4B:
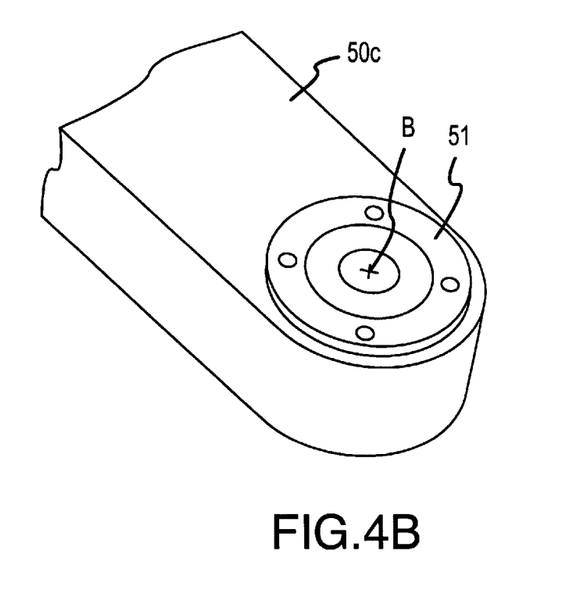
FIG. 4B is a more detailed view of the robot of FIG. 4A taken along lines B—B.
Figure 5:
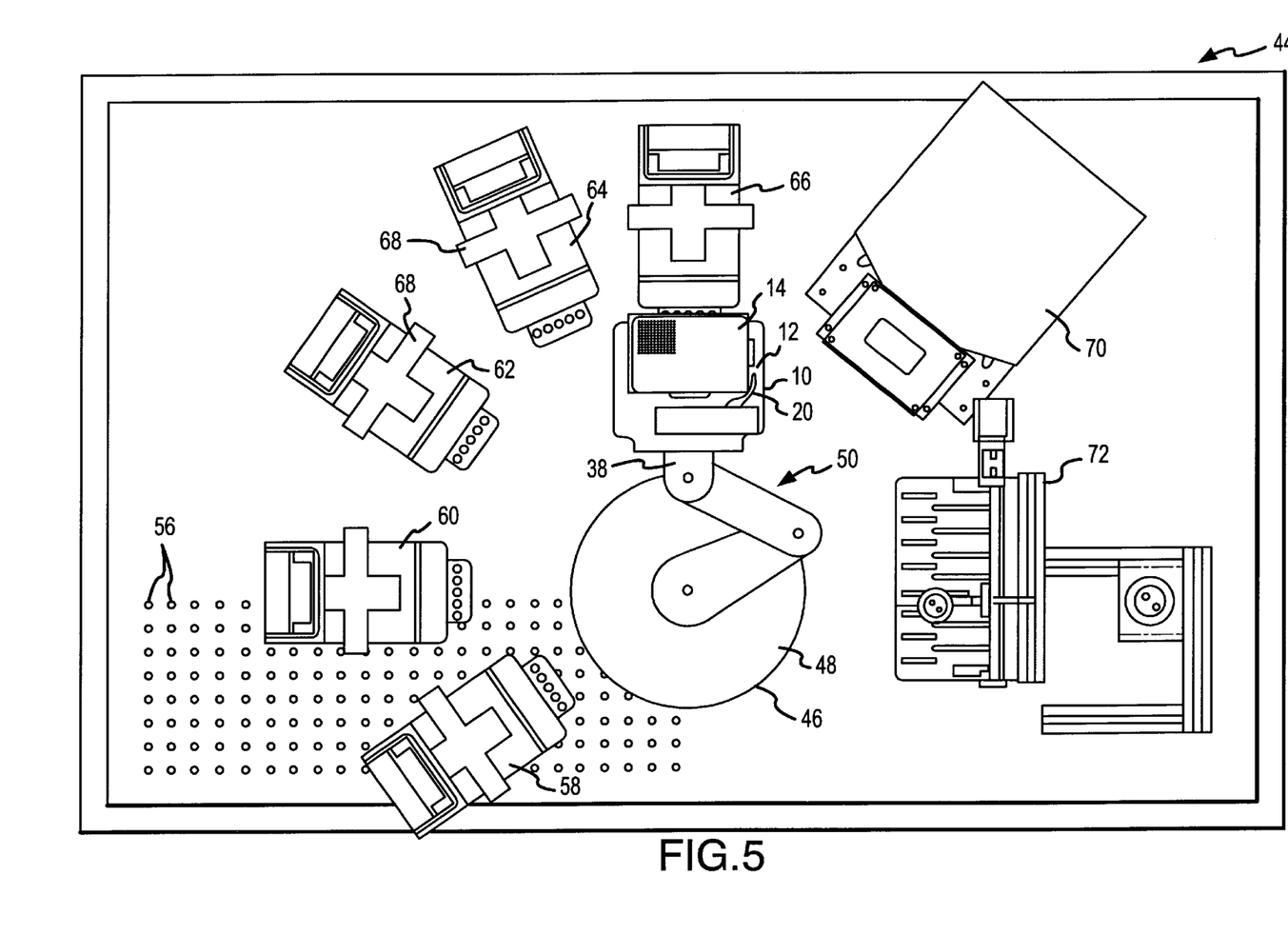
FIG. 5 is a top view of the plate handling system of FIG. 4.
Figure 6:
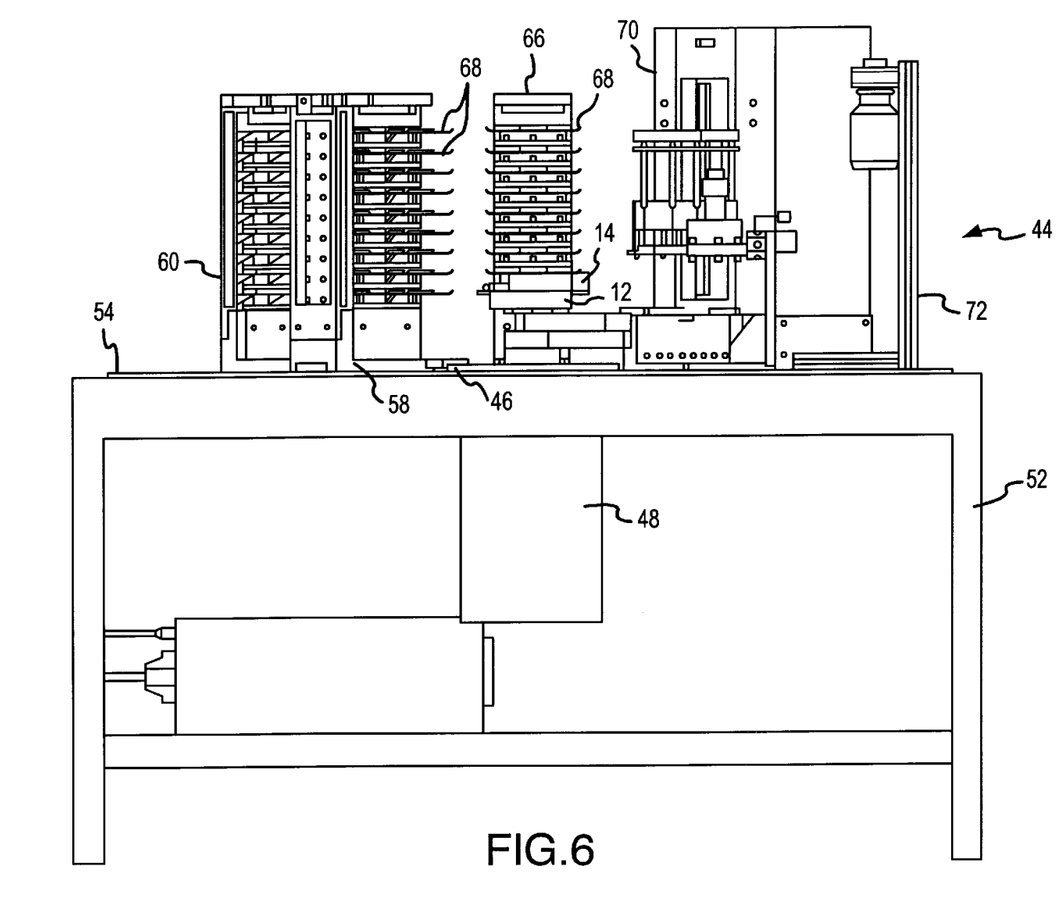
FIG. 6 is a side view of the plate handling system of FIG. 4.

Referring now to FIGS. 4–6, an exemplary work cell 44 will be described. Central to work cell 44 is a robot 46 having a base member 48 and an arm 50. Pivotally attached to arm 50 is grasping mechanism 10. As best shown in FIGS. 4A and 4B, arm 50 comprises a shaft 50a, an elbow 50b, and a linkage 50c. Robot 46 is operably attached to a table 52 having a top 54 which includes a plurality holes 56 (with only a few of holes 56 being shown for convenience of illustration). The distance between each of holes 56 is known so that various pieces of equipment may be attached to top 54, with the distance between the pieces of equipment and robot 46 being known. An exemplary table top which may be used with the invention is a TMC optical table top.

Robot 46 is configured to move in a variety of directions to position plate 14 at various locations. For example, as best shown in FIGS. 4A and 4B, shaft 50a is vertically movable in an up and down motion, i.e. along a Z axis. Shaft 50a is also rotatable relative to base member 48. Elbow 50b is fixedly attached to shaft 50a and rotates with shaft 50a. Linkage 50c is pivotable relative to elbow 50b to allow a distal end of linkage 50c having a turntable 51 to move in a radial direction relative to base member 48. As previously described, frame member 12 is axially translatable relative to attachment member 38. One such robot that may be used with the invention is a ATM-205 robot, commercially available from Equipe Technologies. However, it will be appreciated that other robots may also be used. For example, the invention employ a robot where radial motion is achieved by extension and retraction of a piston.

Figure 4C:
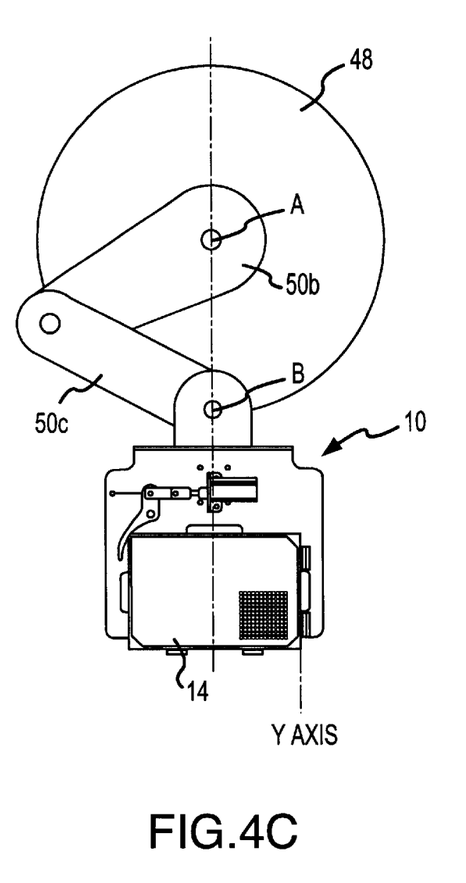
FIGS. 4C and 4D illustrate movement of the robot of FIG. 4.
Figure 4D:
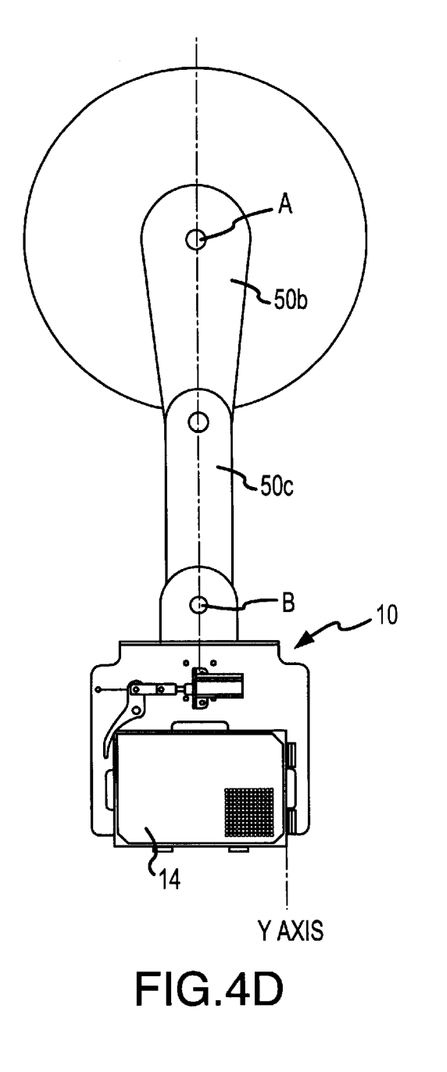

Grasping mechanism 50 is attached to turntable 51 which is configured to maintain a Y axis of plate 14 (see FIGS. 4C and 4D) parallel to a line between points A and B on arm 50 during vertical or rotational movement of shaft 50a and/or during movement of linkage 50c. In this way, turntable 51 will rotate relative to linkage 50c during movement of arm 50 to maintain the Y axis of plate 14 at a constant orientation relative to the line between points A and B. With such a configuration, plate 14 will be properly oriented when moved to various locations surrounding robot 46.

Selectively positioned about table 52 are various pieces of equipment which facilitate the performance of various procedures involving multi-well plate 14. It will appreciated that the particular arrangement illustrated in FIGS. 4–6 is only one type of arrangement, and a variety of other pieces of equipment and/or arrangements may be used in accordance with the principles of the invention. For example, pieces of equipment such as particle dispensers or handlers, fluorimeters, cameras, and the like may be attached to top 54 for performing a variety of procedures including fluid handling, detection, mixing, incubation, depositing of particles (such as beads) in multi-wells plates, and the like.

As shown, attached to top 54 are a plurality of racks 58, 60, 62, 64, and 66. Each of the racks includes a plurality of patterned shelves 68 which are configured to pass through patterned opening 36 of frame member 12 (see FIG. 1) and which are provided to hold multi-well plates. In this manner, robot 46 may be employed to grasp and remove a plate from one of the racks by positioning frame member 12 below one of the shelves 68 which holds a plate that is to be removed. The robot aligns patterned opening 36 with the patterned self 68 and then lifts frame member 12 vertically upward until frame member 12 lifts the plate from the shelf. As previously described, alignment extensions 42 (see FIG. 2) assist in positioning plate 14 onto frame member 12. When plate 14 rests upon frame member 12, air piston 26 (see FIG. 2) is depressurized causing spring 34 to force clamping arm 20 against the corner of plate 14 as previously described. In turn, this forces plate 14 against edges 18 to secure plate 14 to grasping mechanism 10. Robot 46 then moves plate 14 to another one of the racks or another piece of equipment for processing, evaluation, or the like.

Figure 4E:
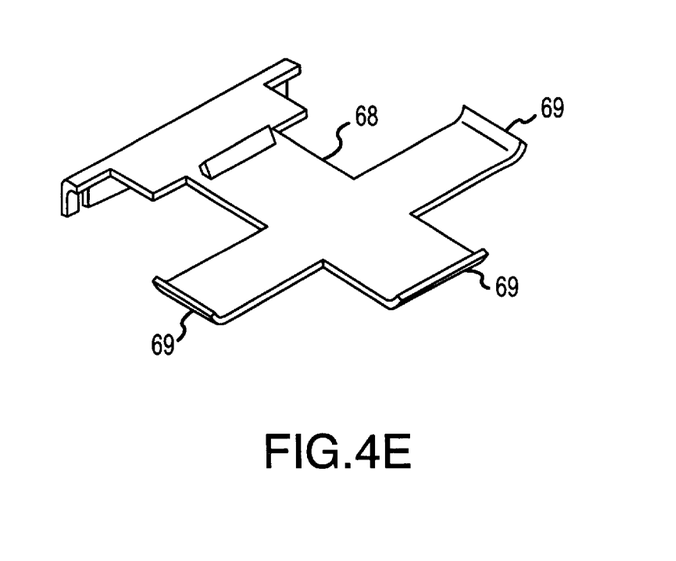
FIG. 4E is a perspective view of a patterned shelf of one of the racks of the system of FIG. 4.

As shown in FIG. 4E, shelf 68 includes raised portions 69 which assist in properly positioning plate 14 on the shelf.

For example, when placing a plate on shelf 68, grasping mechanism 10 is lowered until shelf 68 passes through patterned opening 36. At this point raised portions 69 guide plate 14 onto shelf 68 in a desired orientation.

Robot 46 may be used in performing a variety of procedures. As one example, robot 46 may be employed to move plate 14 to a dispensing station 70. Dispensing station 70 includes an array of dispensing tips or syringes (not shown) for introducing fluids into well 16 of plate 14. For example, dispensing station 70 may comprise a Hydra 96 dispenser, commercially available from Robbins Scientific, which includes a two dimensional array of 96 syringes. With such an arrangement of syringes, robot 46 will move plate 14 to align 96 of its 864 wells with the 96 syringes. After the fluids have been introduced to the 96 wells, the linear translator 40 (see FIG. 1) will linearly translate plate 14 a few millimeters along the X axis to align a group of 96 wells (which are laterally adjacent to the wells just filled) with the 96 syringes. This process is repeated for the next group of wells which are laterally adjacent to the wells just filled. Arm 50 then moves plate 14 so that another set of rows of the wells which are longitudinally spaced from the filled wells are aligned with the syringes. As described above, turntable 51 maintains plate 14 properly oriented along the Y axis during movement of arm 50. The aligned rows are then filled as described above. The above process is then repeated until all of the 864 wells are filled. Hence, by precisely locating 864 wells relative to the frame member, the wells can be accurately filled with 96 syringes.

Adjacent dispensing station 70 is a valve array 72, such as an 8X valve array, having valves which are commercially available from The Lee Company. Robot 46 is employed to move plate 14 to valve array 72, with eight of the wells being aligned with the eight valve array. Array 72 may also be moved by a linear stage to align itself with the columns of wells in plate 14.

Hence, a variety of pieces of equipment may be disposed about robot 46 which is employed to move plate 14 to various stations within the work cell. In turn, various processes and/or evaluation procedures may be performed, with robot 46 facilitating manipulation and handling of plate 14. Since both the location of the wells relative to the robot and the location of the various pieces of equipment relative to the robot are known, the robot may be employed to align the wells with the appropriate pieces of equipment as needed.

Figure 7:
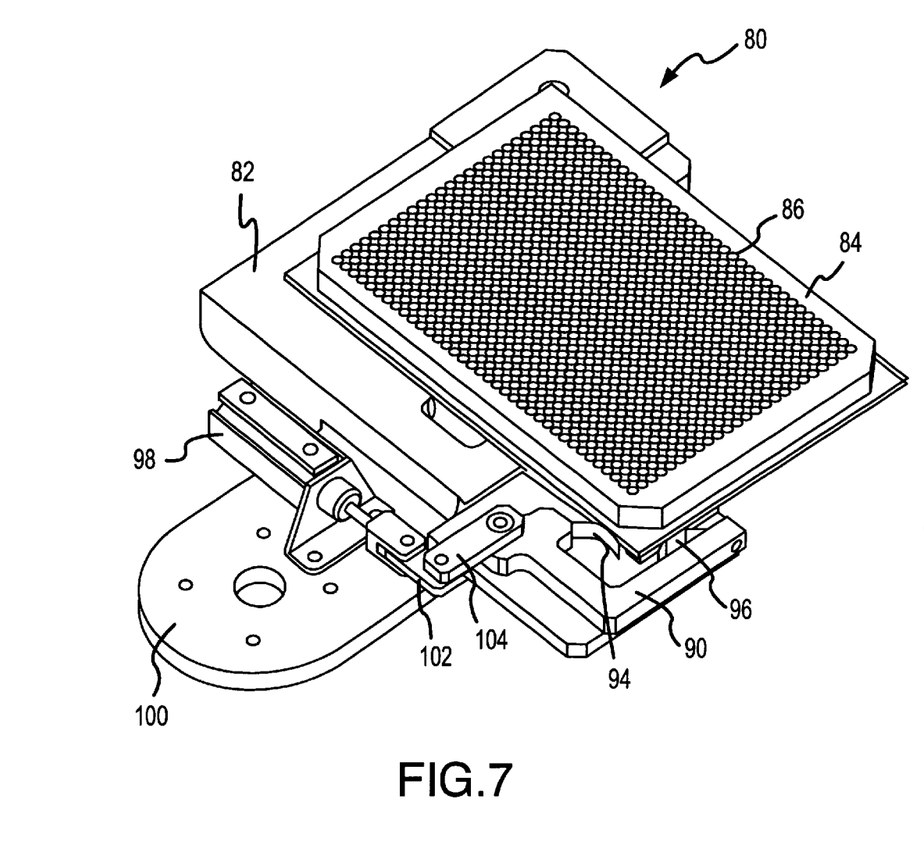
FIG. 7 is a perspective view of an alternative grasping mechanism according to the invention.
Figure 8:
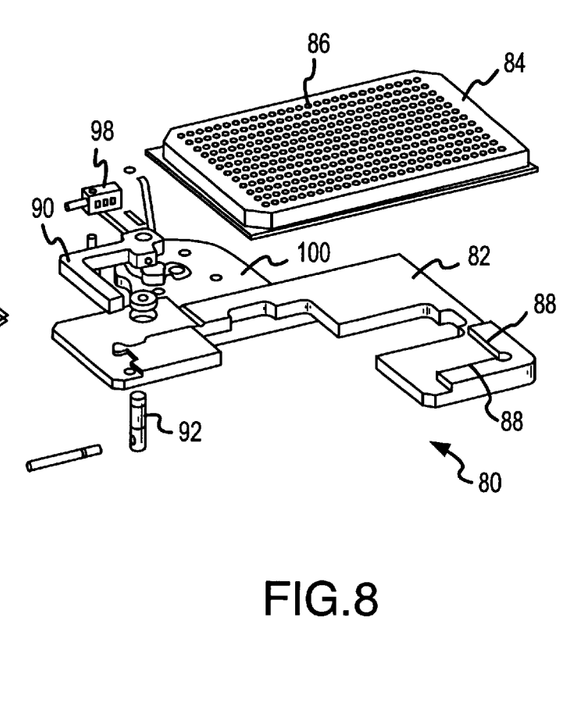
FIG. 8 is an exploded view of the grasping mechanism of FIG. 7.

Referring now to FIGS. 7 and 8, an alternative embodiment of a grasping mechanism 80 will be described.

Grasping mechanism 80 may be employed with a robot in work cell 44 in a manner similar to that previously described. Grasping mechanism 80 comprises a frame member 82 for holding a multi-well plate 84 having a plurality of wells 86. Frame member 82 includes a pair of edges 88 which are perpendicular to each other. A clamping arm 90 is pivotally attached to frame member 82 by a shaft 92. Further, clamping arm 90 includes leaf springs 94 and 96. In this way, when plate 84 is placed on frame member 82, clamping arm 90 is pivoted to force springs 94 and 96 against two sides of plate 84. In turn, the other two sides of plate 84 are forced against edges 88 to secure plate 84 to frame member 82 in a manner similar to that previously described in connection with grasping mechanism 10. An air piston 98 is employed to pivot clamping arm 90. Piston 98 is attached to an attachment member 100 which in turn is configured to attach grasping mechanism 80 to a robot. Various linkages 102 and 104 are positioned between air piston 98 and clamping arm 90 to allow clamping arm 90 to be pivoted upon actuation of air piston 98 in a manner similar to that previously described in connection with grasping mechanism 10.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A system for handling a plate having a plurality of wells, the system comprising:

a robot having a base member and at least one arm and a processor controlling the robot, wherein the processor is configured to control movement of the robot to place the plate at predetermined locations at a plurality of laterally spaced apart stations, wherein the arm includes a grasping mechanism which is adapted to grasp the plate from a rack having a plurality of patterned shelves for housing a plurality of plates, wherein the grasping mechanism is movable by the robot along X, Y, and Z axes, and wherein the grasping mechanism includes a frame member with a patterned opening that corresponds in shape to that of the patterned shelves and is configured to receive the plate from the rack in a repeatable and known location said processor configured to, position the frame member below one of the shelves and upwardly moving the frame member so that such one of the shelves passes through the patterned opening such that the location of each well relative to the grasping mechanism is known by the robot;

said plurality of laterally spaced apart stations at known locations relative to the robot, wherein at least one of the stations includes the rack and at least another of the stations includes equipment operable with a two-dimensional array of wells in the plate, including an array of fluid delivery lines to allow fluids, particles or substances to be introduced into the two-dimensional array of wells or removed from the non-adjacent wells while the plate is grasped by the grasping mechanism.

2. A system as in claim 1, wherein the plate has at least 864 wells, and wherein selective ones of the wells of the plate are aligned with the equipment when the plate is placed at the predetermined locations.

3. A system as in claim 1, wherein the arm comprises a shaft, an elbow attached to the shaft, and a linkage pivotally attached to the elbow, and wherein the grasping mechanism is operably attached to the linkage.

4. A system as in claim 3, wherein the shaft is rotatable relative to the base member and is movable in a vertical direction, and wherein the linkage is pivotable relative to the shaft to move the grasping mechanism radially outward from the base member.

5. A system as in claim 1, wherein the frame member has edges which are adapted to frame at least a portion of a periphery of the plate in a repeatable and predictable manner so that the location of the wells of the plate relative to the frame member is known when the plate is received into the frame member; and a securing mechanism adapted to secure the plate to the frame member when the plate is received within the frame member.

6. A method for handling a plate having a plurality of wells, the method comprising:

providing a robot having a base member and at least one arm, wherein the arm includes a grasping mechanism having a frame member with a patterned opening;

grasping a plate having a plurality of wells from a rack with the grasping mechanism, the rack having a plurality of patterned shelves that correspond in shape to that of the patterned opening for housing a plurality of plates, by positioning the frame member below one of the shelves and upwardly moving the frame member so that such one of the shelves passes through the patterned opening such that the location of each well in the plate relative to the grasping mechanism is known by the robot;

moving the plate with the robot along X, Y and Z axes to a predetermined location at a processing station such that the location of the wells of the plate relative to the station is known; and introducing fluids into or aspirating fluids from a first two-dimensional array of the wells while the plate is at a first predetermined location and while the plate is being grasped by the grasping mechanism.

7. A method as in claim 6, further comprising moving the plate with the robot to a second predetermined location at the processing station and introducing fluids into or aspirating fluids from a second two-dimensional array of the wells.

8. A method as in claim 6, further comprising moving the plate with the robot to a predetermined location at another processing station, and further comprising introducing a biological substance into the first two-dimensional array of wells while the plate is at the predetermined location.

9. A method as in claim 6, further comprising moving the plate with the robot to an evaluation station, and further comprising imaging the first two-dimensional array of wells with a camera while the plate is at the evaluation station.

10. A method as in claim 9, wherein the first two-dimensional array of wells is aligned with pixels of the camera when the plate is at the evaluation station.

11. A method as in claim 6, wherein the plate has at least 864 wells, wherein the first two-dimensional array of wells comprises 96 wells, and further comprising introducing fluids into or aspirating fluids from the two dimensional array of 96 wells.

* * * * *